(12) United States Patent
Evans et al.

(10) Patent No.: US 10,952,855 B2
(45) Date of Patent: Mar. 23, 2021

(54) INFLATABLE PENILE PROSTHESIS WITH REVERSIBLE FLOW PUMP ASSEMBLY

(71) Applicant: Boston Scientific Scimed, Inc., Maple Grove, MN (US)

(72) Inventors: Douglas L. Evans, Andover, MN (US); Karl A. Jagger, Deephaven, MN (US); Mark E. DiLoreto, Chaska, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 174 days.

(21) Appl. No.: 15/462,168

(22) Filed: Mar. 17, 2017

(65) Prior Publication Data

US 2017/0273792 A1 Sep. 28, 2017

Related U.S. Application Data

(60) Provisional application No. 62/312,568, filed on Mar. 24, 2016.

(51) Int. Cl.
*A61F 2/26* (2006.01)

(52) U.S. Cl.
CPC ..................... *A61F 2/26* (2013.01)

(58) Field of Classification Search
CPC ..................... A61F 2/26; A61F 5/41
USPC ..................................... 600/38–41
See application file for complete search history.

(56) References Cited

U.S. PATENT DOCUMENTS

| | | | |
|---|---|---|---|
| 3,100,702 A | 8/1963 | Rauner et al. | |
| 3,832,996 A | 9/1974 | Kalnberz et al. | |
| 3,893,456 A | 7/1975 | Small | |
| 3,954,102 A | 5/1976 | Buuck et al. | |
| 3,987,789 A | 10/1976 | Timm et al. | |
| 3,991,752 A | 11/1976 | Gerow et al. | |

(Continued)

FOREIGN PATENT DOCUMENTS

| | | |
|---|---|---|
| EP | 0137752 B1 | 8/1989 |
| EP | 0774935 B1 | 11/1999 |

(Continued)

OTHER PUBLICATIONS

International Search Report and Written Opinion for PCT Application No. PCT/US2017/023178, dated Jul. 14, 2017, 15 pages.

(Continued)

*Primary Examiner* — John P Lacyk
(74) *Attorney, Agent, or Firm* — Brake Hughes Bellermann LLP

(57) ABSTRACT

According to an aspect, an inflatable penile prosthesis includes an inflatable member, a reservoir configured to hold fluid, and a reversible flow pump assembly configured to facilitate a transfer of the fluid from the reservoir to the inflatable member when in an inflation mode, and facilitate the transfer of the fluid from the inflatable member to the reservoir when in a deflation mode. The reversible flow pump assembly includes a pump, an input check valve coupled to the pump, an output check valve coupled to the pump, and a reversing valve. The input check valve is configured to permit transfer of fluid into the pump. The output check valve is configured to permit transfer of fluid out of the pump. The reversing valve is configured to switch between the inflation mode and the deflation mode.

17 Claims, 5 Drawing Sheets

(56) References Cited

U.S. PATENT DOCUMENTS

| | | | |
|---|---|---|---|
| 4,066,073 A | 1/1978 | Finney et al. | |
| 4,151,840 A | 5/1979 | Barrington et al. | |
| 4,151,841 A | 5/1979 | Barrington et al. | |
| 4,177,805 A | 12/1979 | Tudoriu et al. | |
| 4,187,839 A | 2/1980 | Nuwayser et al. | |
| 4,222,377 A | 9/1980 | Burton et al. | |
| 4,244,370 A | 1/1981 | Furlow et al. | |
| 4,345,339 A | 8/1982 | Mueller et al. | |
| 4,392,562 A | 7/1983 | Burton et al. | |
| 4,411,260 A | 10/1983 | Koss et al. | |
| 4,411,261 A | 10/1983 | Finney et al. | |
| 4,483,331 A | 11/1984 | Trick et al. | |
| 4,517,967 A | 5/1985 | Timm et al. | |
| 4,522,198 A | 6/1985 | Timm et al. | |
| 4,541,420 A | 9/1985 | Timm et al. | |
| 4,588,394 A | 5/1986 | Schulte et al. | |
| 4,594,997 A * | 6/1986 | Hakky | A61F 2/26 600/40 |
| 4,594,998 A | 6/1986 | Porter et al. | |
| 4,619,251 A | 10/1986 | Helms et al. | |
| 4,656,081 A | 4/1987 | Eiichi et al. | |
| 4,665,902 A | 5/1987 | Goff et al. | |
| 4,666,428 A | 5/1987 | Mattioli et al. | |
| 4,669,456 A | 6/1987 | Masters et al. | |
| 4,693,719 A | 9/1987 | Franko et al. | |
| 4,699,128 A | 10/1987 | Hemmeter et al. | |
| 4,881,531 A | 11/1989 | Timm et al. | |
| 4,899,737 A | 2/1990 | Lazarian et al. | |
| 5,048,511 A | 9/1991 | Rosenbluth et al. | |
| 5,050,592 A | 9/1991 | Olmedo et al. | |
| 5,176,708 A | 1/1993 | Frey et al. | |
| 5,283,390 A | 2/1994 | Hubis et al. | |
| 5,445,594 A | 8/1995 | Elist et al. | |
| 5,509,891 A | 4/1996 | Deridder et al. | |
| 5,512,033 A | 4/1996 | Westrum et al. | |
| 5,553,379 A | 9/1996 | Westrum et al. | |
| 5,899,849 A | 5/1999 | Elist et al. | |
| 6,171,233 B1 | 1/2001 | Willard et al. | |
| 6,346,492 B1 | 2/2002 | Koyfman | |
| 6,533,719 B2 | 3/2003 | Kuyava et al. | |
| 6,558,315 B1 | 5/2003 | Kuyava | |
| 6,579,230 B2 | 6/2003 | Yachia et al. | |
| 6,600,108 B1 | 7/2003 | Wijnberg et al. | |
| 6,679,832 B1 | 1/2004 | Sultan | |
| 6,723,042 B2 | 4/2004 | Almli et al. | |
| 6,730,017 B2 | 5/2004 | Kuyava et al. | |
| 6,935,847 B2 | 8/2005 | Kuyava et al. | |
| 6,953,429 B2 | 10/2005 | Forsell et al. | |
| 6,991,601 B2 | 1/2006 | Kuyava et al. | |
| 6,991,604 B2 | 1/2006 | Cantrell | |
| 7,350,538 B2 | 4/2008 | Kuyava et al. | |
| 7,407,482 B2 | 8/2008 | Kuyava et al. | |
| 7,438,682 B2 | 10/2008 | Kuyava et al. | |
| 7,442,165 B2 * | 10/2008 | Forsell | A61F 2/26 600/38 |
| 7,481,763 B2 | 1/2009 | Hassler et al. | |
| 7,637,861 B2 | 12/2009 | Kuyava et al. | |
| 7,717,845 B2 | 5/2010 | George et al. | |
| 7,874,978 B2 | 1/2011 | Kuyava et al. | |
| 7,914,439 B2 | 3/2011 | Kuyava et al. | |
| 7,963,909 B2 | 6/2011 | George et al. | |
| 8,016,746 B2 | 9/2011 | Ellering | |
| 8,062,209 B2 | 11/2011 | Rowland et al. | |
| 8,109,870 B2 | 2/2012 | Kuyava et al. | |
| 8,167,788 B2 | 5/2012 | Arp et al. | |
| 8,241,203 B2 | 8/2012 | Fogarty | |
| 8,257,246 B1 | 9/2012 | Fogarty | |
| 8,276,591 B2 | 10/2012 | Henkel et al. | |
| 8,337,392 B2 | 12/2012 | Morningstar | |
| 8,491,462 B2 | 7/2013 | Chechik | |
| 8,517,916 B2 | 8/2013 | Ellering | |
| 8,523,761 B2 | 9/2013 | Ellering | |
| 8,545,393 B2 | 10/2013 | Ellering | |
| 8,568,294 B2 | 10/2013 | Ellering | |
| 8,617,052 B2 | 12/2013 | Fogarty | |
| 8,632,456 B2 | 1/2014 | Fogarty et al. | |
| 8,641,601 B2 | 2/2014 | Ellering | |
| 8,684,910 B2 | 4/2014 | Chechik | |
| 8,740,769 B2 | 6/2014 | Chechik | |
| 8,740,771 B2 | 6/2014 | Ellering | |
| 8,801,594 B2 | 8/2014 | Fogarty | |
| 8,932,203 B2 | 1/2015 | Ellering | |
| 8,932,204 B2 | 1/2015 | Fogarty et al. | |
| 8,939,890 B2 | 1/2015 | Morningstar | |
| 8,951,186 B2 | 2/2015 | Ellering | |
| D725,271 S | 3/2015 | Chechik | |
| 8,974,370 B2 | 3/2015 | Chechik | |
| 9,017,245 B2 | 4/2015 | Forsell | |
| 9,089,426 B2 | 7/2015 | Henkel et al. | |
| 9,101,474 B2 | 8/2015 | Derus | |
| 9,186,251 B2 | 11/2015 | Fogarty et al. | |
| 9,308,088 B2 | 4/2016 | Chechik | |
| 9,554,937 B2 | 1/2017 | Daniel | |
| 9,649,217 B2 | 5/2017 | Daniel | |
| 9,795,484 B2 | 10/2017 | Daniel | |
| 9,814,554 B2 | 11/2017 | McClurg | |
| 9,877,834 B2 | 1/2018 | Vaingas et al. | |
| 9,907,653 B2 | 3/2018 | Taylor | |
| 9,956,079 B2 | 5/2018 | Daniel | |
| 9,987,136 B2 | 6/2018 | Daniel | |
| 9,999,508 B2 | 6/2018 | Darnell et al. | |
| 10,098,741 B2 | 10/2018 | Wolf | |
| 10,285,815 B2 | 5/2019 | Henkel et al. | |
| 10,327,902 B2 | 6/2019 | Forsell | |
| 10,383,730 B2 | 8/2019 | Daniel | |
| 10,682,233 B2 | 6/2020 | Wolf | |
| 10,722,367 B2 | 7/2020 | Kansas et al. | |
| 10,729,547 B2 | 8/2020 | Darnell et al. | |
| 2003/0114729 A1 | 6/2003 | Forsell | |
| 2003/0144648 A1 | 7/2003 | Forsell et al. | |
| 2004/0098113 A1 | 5/2004 | Forsell et al. | |
| 2005/0014993 A1 | 1/2005 | Mische et al. | |
| 2005/0113638 A1 | 5/2005 | Kuyava et al. | |
| 2005/0267500 A1 | 12/2005 | Hassler et al. | |
| 2007/0142700 A1 | 6/2007 | Fogarty et al. | |
| 2008/0103353 A1 | 5/2008 | Jahns et al. | |
| 2009/0105818 A1 | 4/2009 | George et al. | |
| 2009/0171375 A1 | 7/2009 | Coe et al. | |
| 2010/0185049 A1 | 7/2010 | Birk et al. | |
| 2011/0201875 A1 | 8/2011 | Stroumpoulis et al. | |
| 2011/0201880 A1 * | 8/2011 | Fogarty | A61F 2/26 600/40 |
| 2011/0208229 A1 | 8/2011 | Snow et al. | |
| 2011/0306824 A1 | 12/2011 | Perron et al. | |
| 2012/0003108 A1 | 1/2012 | Ozaki et al. | |
| 2012/0296158 A1 | 11/2012 | Fogarty | |
| 2015/0276690 A1 | 10/2015 | Hudalla et al. | |
| 2018/0064519 A1 | 3/2018 | Wirbisky et al. | |
| 2018/0214271 A1 | 8/2018 | Poucher et al. | |
| 2018/0214272 A1 | 8/2018 | List | |
| 2018/0289489 A1 | 10/2018 | Akky | |
| 2019/0000626 A1 | 1/2019 | Tal et al. | |
| 2020/0146827 A1 | 5/2020 | Allen et al. | |
| 2020/0155319 A1 | 5/2020 | Allen et al. | |

FOREIGN PATENT DOCUMENTS

| | | |
|---|---|---|
| EP | 1255513 B1 | 5/2005 |
| EP | 1670393 B1 | 9/2009 |
| EP | 2272465 A1 | 1/2011 |
| EP | 2391302 A1 | 12/2011 |
| EP | 2391307 A1 | 12/2011 |
| EP | 2531144 B1 | 6/2014 |
| EP | 2767261 A1 | 8/2014 |
| EP | 2805689 A1 | 11/2014 |
| EP | 1962745 B1 | 9/2015 |
| EP | 2501339 B1 | 2/2016 |
| EP | 2839809 B1 | 5/2016 |
| EP | 2741712 B1 | 6/2016 |
| EP | 2957263 B1 | 9/2016 |
| EP | 2965719 B1 | 10/2016 |
| EP | 3123981 A1 | 2/2017 |
| EP | 3135250 A1 | 3/2017 |
| EP | 2747710 B1 | 4/2017 |

(56) References Cited

FOREIGN PATENT DOCUMENTS

| | | |
|---|---|---|
| EP | 3150175 A1 | 4/2017 |
| EP | 3222249 A1 | 9/2017 |
| EP | 3242631 A1 | 11/2017 |
| EP | 2696808 B1 | 7/2018 |
| EP | 2415422 B1 | 8/2018 |
| EP | 3384875 A1 | 10/2018 |
| EP | 3393402 A1 | 10/2018 |
| EP | 3028673 B1 | 7/2019 |
| EP | 3001980 B1 | 11/2019 |
| EP | 3563807 A1 | 11/2019 |
| EP | 3574870 A1 | 12/2019 |
| GB | 2151484 A | 7/1985 |
| JP | H07184940 A | 7/1995 |
| JP | H11509457 A | 8/1999 |
| KR | 101131148 B1 | 3/2012 |
| WO | 8601398 A1 | 3/1986 |
| WO | 9604854 A1 | 2/1996 |
| WO | 9634581 A1 | 11/1996 |
| WO | 2013020555 A2 | 2/2013 |
| WO | 2014123408 A1 | 8/2014 |
| WO | 2015093681 A1 | 6/2015 |

OTHER PUBLICATIONS

Notice of Allowance for Japanese Application No. 2018-568185, dated Aug. 11, 2020, 6 pages.

* cited by examiner

INFLATABLE PENILE PROSTHESIS WITH REVERSIBLE FLOW PUMP ASSEMBLY

CROSS-REFERENCE TO RELATED APPLICATION

This application is a Nonprovisional of, and claims priority to, U.S. Patent Application No. 62/312,568, filed on Mar. 24, 2016, entitled "INFLATABLE PENILE PROSTHESIS WITH REVERSIBLE FLOW PUMP ASSEMBLY", which is incorporated by reference herein in its entirety.

TECHNICAL FIELD

This disclosure relates to an inflatable penile prosthesis with a reversible flow pump assembly and methods for operating the same.

BACKGROUND

One common treatment for male erectile dysfunction is the implantation of a penile prosthesis that mechanically erects the penis. According to some existing designs of inflatable penile prostheses, the amount of time, energy and disparity from the occurrence of a normal human male erection for the patient to inflate a penile prosthesis (e.g., the number of pumps and time required to provide the desired penis rigidity) may be relatively high, and additionally transitioning to the deflation state may be relatively cumbersome.

SUMMARY

According to an aspect, an inflatable penile prosthesis includes an inflatable member, a reservoir configured to hold fluid, and a reversible flow pump assembly configured to facilitate a transfer of the fluid from the reservoir to the inflatable member when in an inflation mode, and facilitate the transfer of the fluid from the inflatable member to the reservoir when in a deflation mode. The reversible flow pump assembly includes a pump, an input check valve coupled to the pump, an output check valve coupled to the pump, and a reversing valve. The input check valve is configured to permit transfer of fluid into the pump. The output check valve is configured to permit transfer of fluid out of the pump. The reversing valve is configured to switch between the inflation mode and the deflation mode.

According to some aspects, the inflatable penile prosthesis may include one or more of the following features (or any combination thereof). When the reversing valve is in the inflation mode, the reservoir may be fluidly coupled to an inlet of the input check valve, and the inflatable member may be fluidly coupled to an outlet of the output check valve. When the reversing valve is in the deflation mode, the reservoir may be fluidly coupled to an outlet of the output check valve, and the inflatable member may be coupled to an inlet of the input check valve. The reservoir may be pressurized such that activation of the reversing valve to the inflation mode causes at least a portion of the fluid to transfer from the reservoir to the inflatable member through the reversible flow pump assembly without operating the pump. When the reversing valve is in the inflation mode, the pump may be configured to be depressed causing the fluid to transfer from the reservoir to the inflatable member through the reversible flow pump assembly. The activation of the reversing valve to the deflation mode may cause at least a portion of the fluid to transfer from the inflatable member to the reservoir through the reversible flow pump assembly without operating the pump. When the reversing valve is in the deflation mode, the pump may be configured to be depressed causing the fluid to transfer from the inflatable member to the reservoir through the reversible flow pump assembly. The inflatable member may include at least two cylinders. The input check valve may include a one-directional pressure valve. The output check valve may include a one-directional pressure valve. The reversing valve may include a first port coupled to an inlet of the input check valve, a second port coupled to an outlet of the output check valve, a third port fluidly coupled to the reservoir, and a fourth port fluidly coupled to the inflatable member. When the reversing valve is in the inflation mode, the reversing valve may provide a first flow connection between the third port to the first port such that the fluid can be transferred from the reservoir into the pump via the first flow connection and the input check valve, and a second flow connection between the second port and the fourth port such that the fluid can be transferred from the pump to the inflatable member via the output check valve and the second flow connection. When the reversing valve is switched to the deflation mode, the reversing valve may be configured to switch the first and second flow connections such that the inflatable member is within fluid communication with the input check valve and the output check valve is within fluid communication with the reservoir. The pump may include a pump bulb. The reservoir may include a biasing member configured to pressurize the reservoir.

According to an aspect, an inflatable penile prosthesis may include an inflatable member, a pressurized reservoir configured to hold fluid, and a reversible flow pump assembly configured to facilitate a transfer of the fluid from the reservoir to the inflatable member when in an inflation mode, and facilitate the transfer of fluid from the inflatable member to the reservoir when in a deflation mode. When the reversible flow pump is activated to the inflation mode, at least a portion of the fluid can automatically be transferred from the pressurized reservoir to the inflatable member through the reversible flow pump assembly.

According to some aspects, the inflatable penile prosthesis may include one or more of the above and/or below features (or any combination thereof). The fluid may transfer from the pressurized reservoir to the inflatable member until fluid pressure substantially equalizes between the pressurized reservoir and the inflatable member. The reversible flow pump assembly may include a pump, an input check valve coupled to the pump, where the input check valve is configured to permit transfer of fluid into the pump, an output check valve coupled to the pump, where the output check valve is configured to permit the transfer of fluid out of the pump, and a reversing valve configured to switch between the inflation mode and the deflation mode. When the reversing valve is in the inflation mode, the reservoir may be fluidly coupled to the input check valve, and the inflatable member may be fluidly coupled to the output check valve. When the reversing valve is in the deflation mode, the reservoir may be fluidly coupled to the output check valve, and the inflatable member may be fluidly coupled to the input check valve.

According to an aspect, a method for operating an inflatable penile prosthesis includes operating a reversing valve to place a reversible flow pump assembly in an inflation mode, where the reversible flow pump assembly includes a pump, an input check valve, and an output check valve, transferring fluid within a reservoir to the pump via the input check valve, and transferring the fluid within the pump to an inflatable member via the output check valve.

According to some aspects, the method may further include operating the reversing valve to place the reversible flow pump assembly in a deflation mode such that flow connections of the reversing valve are reversed, transferring the fluid within the inflatable member to the pump via the input check valve, and transferring the fluid within the pump to the reservoir via the output check valve. At least a portion of the fluid may be transferred from the reservoir to the inflatable member via the reversible flow pump assembly without operating the pump.

DETAILED DESCRIPTION

Figure 1:
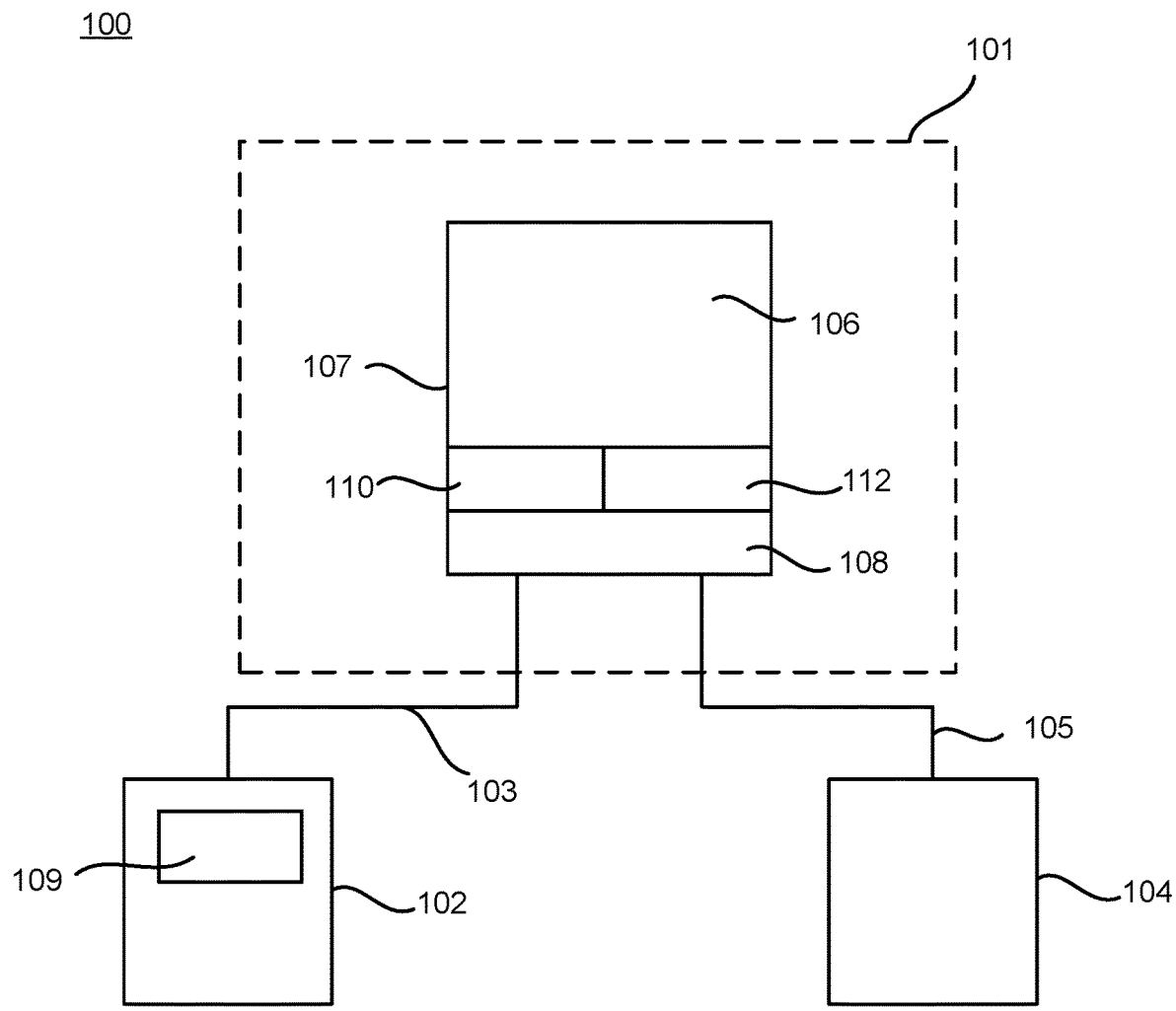
FIG. 1 schematically illustrates an inflatable penile prosthesis having a reversible flow pump assembly according to an aspect.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are to medical devices (e.g., penile prostheses), methods of making medical devices, procedures for placing medical devices within a body of a patient, and methods for operating the medical devices. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

The terms proximal and distal described in relation to various devices, apparatuses, and components as discussed in the subsequent text of the present disclosure are referred with a point of reference. The point of reference, as used in this description, is a perspective of a person who implants the inflatable penile prosthesis. The person may be a surgeon, a physician, a nurse, a doctor, a technician, and the like who may perform the implantation procedure. The term proximal refers to an area or portion that is closer or closest to the person during the implantation procedure. The term distal refers to an area or portion that is farther or farthest from the person.

The embodiments discussed herein may simply the mechanism of selecting fluidic flow orientation, thereby increasing the number of patients that could successfully operate the erect/flaccid state control interface as well as increasing the reliability of the system.

The embodiments include an inflatable penile prosthesis having a reversible flow pump assembly, an inflatable member, and a reservoir. The inflatable member may be implanted into the corpus cavernosae of a user, the reservoir may be implanted in the user's abdomen, and the reversible flow pump assembly may be implanted in the scrotum. In some examples, the reservoir may be pressurized. During use, the user may place the reversible flow pump assembly within an inflation mode which may cause fluid to be automatically transferred from the reservoir through the reversible flow pump assembly to the inflatable member (e.g., due to pressure within the reservoir being greater than the inflatable member), which may result in the at least partial inflation of the inflatable member. Then, the user may actuate a pump of the reversible flow pump assembly to further transfer the fluid from the reservoir to the inflatable member, to provide the desired penis rigidity for a normal erection. In some examples, the automatic transfer to fluid to the inflatable member may cause a reduction in the amount of pumps to provide the desired penis rigidity. Also, with added pressure to the reservoir, the pump can be filled at a faster rate.

Then, when the user desires to deflate the inflatable member, the user may switch the reversible flow pump assembly to a deflation mode, and the pump of the reversible flow pump assembly may be pumped to transfer the fluid from the inflatable member to the reservoir, which returns the penis to a flaccid state. Besides the pump, the reversible flow pump assembly may also include a reversing valve with two one-way check valves in order to switch the flow direction between an inflation direction in which the fluid is transferred from the reservoir to the inflatable member and a deflation direction in which the fluid is transferred from the inflatable member to the reservoir. For instance, the user may operate a mode actuator (e.g., user-operated button or other type of actuator) on the reversing valve to change from the inflation mode to the deflation mode, which causes the connections to the two one-way check valves to be reversed, thereby enabling a reversible flow pump.

FIG. 1 schematically illustrates an inflatable penile prosthesis 100 according to an aspect. The inflatable penile prosthesis 100 may include a reservoir 102, an inflatable member 104, and a reversible flow pump assembly 101 may transfer fluid between the reservoir 102 and the inflatable member 104. In some examples, the inflatable member 104 may be implanted into the corpus cavernosae of the user, the reservoir 102 may be implanted in the abdomen or pelvic cavity of the user (e.g., the reservoir 102 may be implanted in the lower portion of the user's abdominal cavity or the upper portion of the user's pelvic cavity), and the reversible flow pump assembly 101 may be implanted in the scrotum of the user.

The inflatable member 104 may include one or more elongate members capable of expanding upon the injection of fluid into a cavity of the inflatable member 104. For instance, upon injection of the fluid into the inflatable member 104, the inflatable member 104 may increase its length and/or width, as well as increase its rigidity. In some examples, the inflatable member 104 may include a pair of cylinders or at least two cylinders, e.g., a first cylinder member and a second cylinder member. In some examples, each cylinder may include a cylindrical silicone rubber body or sleeve which, owing to its resiliency, is expandable circumferentially and also longitudinally. The volumetric capacity of the inflatable member 104 may depend on the size of the cylinders. In some examples, the volume of fluid in each cylinder may vary from about 10 milliliters in smaller cylinders and to about 50 milliliters in larger sizes. Further details of the cylinders are further explained with reference to FIGS. 2-3.

The reservoir 102 may include a container having an internal chamber configured to hold fluid that is used to inflate the inflatable member 104. The volumetric capacity of the reservoir 102 may vary depending on the size of the inflatable penile prosthesis 100. In some examples, the volumetric capacity of the reservoir 102 may be 40-50 cubic centimeters. In some examples, the reservoir 102 is constructed from the same material as the inflatable member 104. In other examples, the reservoir 102 is constructed from a different material than the inflatable member 104.

In some examples, the reservoir 102 may be pressurized. In some examples, the reservoir 102 is pressurized less than or equal to a pressurized threshold. In some examples, the reservoir 102 is pressurized to be equal to or less than diastolic pressure in order to ensure that the reservoir 102 is not over pressurized. In some examples, the pressurized threshold is 70 mm/Hg. In some examples, the pressurized threshold is greater than 70 mm/Hg. In other examples, the pressurized threshold is less than 70 mm/Hg. In some examples, the reservoir 102 includes a pressure regulating balloon. In other examples, the reservoir 102 is not pressurized (e.g., static). In some examples, reservoir 102 may include a single container configured to hold the fluid, which may or may not be pressurized. In some examples, the reservoir 102 includes a primary container (or primary chamber) and a secondary container (or secondary chamber), where the primary container/chamber may hold the fluid that is transferred to the inflatable member 104, and the secondary container/chamber may include gas or secondary fluid that is used to pressurize the fluid in the primary container/chamber.

In some examples, the reservoir 102 may include a biasing member 109 configured to pressurize the fluid in the reservoir 102. For example, upon injection of fluid into the reservoir 102, the biasing member 109 may provide a force on the fluid, thereby pressurizing the reservoir 102. The biasing member 109 may be biased to an original size or position, and the biasing member 109 may expand to a different size or position when the fluid is injected into the reservoir 102 and/or the biasing member 109, thereby creating a pressurized reservoir 102. In some examples, the biasing member 109 may include a spring or a spring-loaded assembly that biases the reservoir 102 to a particular size or position. In some examples, the biasing member 109 may be an expandable balloon inside a more rigid container of the reservoir 102. For instance, the expandable balloon may be biased to a smaller size when it is not filled with fluid. Then, upon injection of the fluid into the expandable balloon, the expandable balloon may expand and pressurize the fluid contained therein. In some examples, the biasing member 109 may be a biased diaphragm, which may be a membrane, flap, or other structure contained within the reservoir 102 that may separate one area of the reservoir 102 from another area of the reservoir 102. The diaphragm may be biased to an original position. Upon injection of the fluid into the reservoir 102, the diaphragm may flex, expand, or move to account for the increased fluid such that the fluid can be pressurized within the reservoir 102. In other examples, the reservoir 102 may be constructed from a substantially elastic walled abdominal conforming member. For example, the reservoir 102 may be located in in the abdomen within the space of retzius (retropubic space) or other sub-muscular locations, and the reservoir 102 may pre-charged or pressurized (to at least two or three psi) ahead of the desired moment of transformation of the penis from flaccid to erect due to the substantially elastic walled abdominal conforming member.

The inflatable penile prosthesis 100 may include a first conduit connector 103 and a second conduit connector 105. Each of the first conduit connector 103 and the second conduit connector 105 may define a lumen configured to transfer the fluid to and from the reversible flow pump assembly 101. The first conduit connector 103 may be coupled to the reversible flow pump assembly 101 and the reservoir 102 such that fluid can be transferred between the reversible flow pump assembly 101 and the reservoir 102 via the first conduit connector 103. For example, the first conduit connector 103 may define a first lumen configured to transfer fluid between the reversible flow pump assembly 101 and the reservoir 102. The first conduit connector 103 may include a single or multiple tube members for transferring the fluid between the reversible flow pump assembly 101 and the reservoir 102.

The second conduit connector 105 may be coupled to the reversible flow pump assembly 101 and the inflatable member 104 such that fluid can be transferred between the reversible flow pump assembly 101 and the inflatable member 104 via the second conduit connector 105. For example, the second conduit connector 105 may define a second lumen configured to transfer fluid between the reversible flow pump assembly 101 and the inflatable member 104. The second conduit connector 105 may include a single or multiple tube members for transferring the fluid between the reversible flow pump assembly 101 and the inflatable member 104. In some examples, the first conduit connector 103 and the second conduit connector 105 may include a silicone rubber material.

The reversible flow pump assembly 101 may switch between an inflation mode in which the fluid in the reservoir 102 is transferred to the inflatable member 104 through the reversible flow pump assembly 101 in a first direction (e.g., inflation direction) and a deflation mode in which the fluid in the inflatable member 104 is transferred back to the reservoir 102 through the reversible flow pump assembly 101 in a second direction (e.g., deflation direction). The reversible flow pump assembly 101 may include a reversing valve 108, an input check valve 110, and an output check valve 112, in order to move fluid in either the inflation direction or the deflation direction.

The reversible flow pump assembly 101 may include a pump 106 configured to be pumped by the user in order to facilitate the transfer of fluid from the reservoir 102 to the inflatable member 104, and in the reverse direction from the inflatable member 104 to the reservoir 102. For example, in the inflation mode, the pump 106 may receive the fluid from the reservoir 102, and then output the fluid to the inflatable member 104. In the deflation mode, the pump 106 may receive the fluid from the inflatable member 104, and then output the fluid to the reservoir 102. In some examples, the pump 106 may include a flexible member defining a cavity (e.g., a pump bulb). In some examples, the pump 106 may include a squeeze pump. In some examples, the pump 106 may be round or substantially round. In some examples, the pump 106 may include ribbing or dimples to aid the user in gripping the pump 106. The pump 106 may use suction and pressure to move the fluid in and out of the cavity of the pump 106. For example, the user may depress or squeeze the pump 106 to expel the fluid out of the cavity, and, when the flexible member returns to its original shape, the resulting suction pushes the fluid into the cavity of the pump 106. In some examples, the pump 106 may have a bulb spring rate that is designed to refill the pump 106 in a selected time frame. In some examples, the bulb spring rate (especially in the completely flattened state of the squeezed pump bulb) may be selectively enhanced to create a vacuum by the addition of a nitinol spring configured as a sphere that exerts opening force on the bulb walls. This spring could also be designed such that it does not substantially increase the compressive squeeze force required to expel fluid out of the bulb in the opened state through the use of hinge/buckle points.

The reversible flow pump assembly 101 may include a housing 107 configured to enclose the pump 106, the input check valve 110, the output check valve 112, and the reversing valve 108. In some examples, the housing 107 may include a unitary structure designed to enclose the pump 106, the input check valve 110, the output check valve 112, and the reversing valve 108. The housing 107 may encompass a wide variety of different shapes and sizes. In some examples, the housing 107 includes a polymer-based material. In some examples, the housing 107 includes a polymer-based material incased within silicon. In other examples, the housing 107 may include two or more housing structures designed to enclose the pump 106, the input check valve 110, the output check valve 112, and the reversing valve 108. In some examples, the valve components (e.g., the input check valve 110, the output check valve 112, and the reversing valve 108) are contained within a rigid, dimensionally stable, and/or tightly toleranced insert surrounded by anatomically representative compliant materials enabling repeatable actuation of the internal valve components while maintaining patient comfort outwardly within the scrotum.

The input check valve 110 may be coupled to the pump 106. The input check valve 110 may include an inlet that receives fluid from a source (e.g., the reservoir 102 via the first conduit connector 103 or the inflatable member 104 via the second conduit connector 105), and an outlet that is coupled to the pump 106. In some examples, the input check valve 110 may be directly coupled to an opening on the pump 106. In other examples, the input check valve 110 may be indirectly coupled to the opening on the pump 106. The input check valve 110 may be the only passageway in which the fluid can flow into the pump 106. The input check valve 110 may include any mechanical valve that permits the flow of fluid in one direction (from the inlet to the outlet) (e.g., one-way directional valve). The input check valve 110 may be coupled to the pump 106 such that fluid can only flow into the pump 106 via the input check valve 110. The input check valve 110 may block the flow of fluid out of the pump 106 via the input check valve 110.

In some examples, the input check valve 110 may have a closed state and an open state, and the opening or closing of the input check valve 110 is based on the pressure applied to the input check valve 110 (e.g., the input check valve 110 may be a pressure valve). For example, in the closed state, the input check valve 110 may restrict or block fluid from entering the pump 106 via the input check valve 110, but, when the pressure is equal to or exceeds a threshold level, the input check valve 110 may transition to the open state in which fluid can be transferred into the pump 106 via the input check valve 110. In some examples, the input check valve 110 may include a duckbill valve. For example, the duckbill valve may include a flattened (or substantially flattened) end portion at its outlet, and, when the pressure is greater than a threshold amount, the flattened end portion is configured to open to permit the fluid to pass. When the pressure is removed, the duckbill end may return to its flattened shape, preventing backflow. However, the input check valve 110 may include other types of valves such as a diaphragm check valve, a swing check valve, a tilting disc check valve, a stop-check valve, a lift-check valve, or an in-line check valve.

The output check valve 112 may be coupled to the pump 106. The output check valve 112 may include an inlet that receives fluid from the pump 106 and an outlet coupled to a destination (e.g., the reservoir 102 via the first conduit connector 103 or the inflatable member 104 via the second conduit connector 105). The output check valve 112 may be the only passageway in which the fluid can flow out of the pump 106. The output check valve 112 may include any mechanical valve that permits the flow of fluid in one direction (from the inlet to the outlet) (e.g., one-way directional valve). The output check valve 112 may be coupled to the pump 106 such that fluid can only flow out of the pump 106 via the output check valve 112. In some examples, the output check valve 112 may have a closed state and an open state, and the opening or closing of the output check valve 112 is based on the pressure applied to the output check valve 112 (e.g., the output check valve 112 may be a pressure valve). For example, in the closed state, the output check valve 112 may restrict or block fluid from exiting the pump 106 via the output check valve 112, but, when the pressure is equal to or exceeds a threshold level, the output check valve 112 may transition to the open state in which fluid can be transferred out of the pump 106 via the output check valve 112. In some examples, the output check valve 112 may include a duckbill valve, as explained above. However, the output check valve 112 may include other types of valves such as a diaphragm check valve, a swing check valve, a tilting disc check valve, a stop-check valve, a lift-check valve, or an in-line check valve.

The input check valve 110 and the output check valve 112 may have the same type of valve. In other examples, the input check valve 110 may be a different type than the output check valve 112. In some examples, the reversible flow pump assembly 101 may include one or more filters. For example, a filter may be disposed on the inlet of the input check valve 110 and/or the inlet of the output check valve 112.

The reversing valve 108 may be any type of device for controlling the passage of fluid through the reversible flow pump assembly 101. The reversible flow pump assembly 101 provides both inflation and deflation control by activating the reversing valve 108. The reversing valve 108 may be coupled to the inlet of the input check valve 110 and the outlet of the output check valve 112. The reversing valve 108 may be coupled to the reservoir 102 via the first conduit connector 103. The reversing valve 108 may be coupled to the inflatable member 104 via the second conduit connector 105.

The reversing valve 108 may control the connections to the inlet of the input check valve 110 and the outlet of the output check valve 112, thereby controlling the direction in which the fluid is transferred. For instance, the reversing valve 108 may control which component (e.g., the reservoir 102 or the inflatable member 104) is fluidly coupled to the inlet of the input check valve 110 and which component (e.g., the reservoir 102, or the inflatable member 104) is fluidly coupled to the outlet of the output check valve 112.

The reversing valve 108 may have a first position in which the reversible flow pump assembly 101 is in the inflation mode, and a second position in which the reversible flow pump assembly 101 is in the deflation mode. In some examples, the reversing valve 108 may include a user-operated control such as a button, switch, etc. to control whether it is within the inflation mode or the deflation mode. The user may operate the reversing valve 108 to switch between the first position and the second position. In other examples, the reversing valve 108 may include more than two positions (e.g., a third position that corresponds to neither the inflation mode nor the deflation mode). In some examples, the reversing valve 108 may include a spool valve that allows the flow of fluid into different paths from the reservoir 102 and the inflatable member 104. In some examples, the reversing valve 108 configured as the spool valve may include a spool inside a cylinder which is mechanically (or electrically controlled), where the movement of the spool restricts or permits the flow to and from a particular source and destination.

When the user wishes to inflate the inflatable member 104, the user may operate the reversing valve 108 to switch to the first position (e.g., the inflation mode). In the first position, the reversing valve 108 may provide an open connection between the reservoir 102 and the inlet of the input check valve 110, and an open connection between the outlet of the output check valve 112 and the inflatable member 104. In the first position, if the reservoir 102 is at least partially pressurized, the fluid may automatically flow out of the reservoir 102 and into the inflatable member 104 without the user depressing or squeezing the pump 106 until the pressure is at least partially equalized between the reservoir 102 and the inflatable member 104.

In particular, after the reversing valve 108 is switched to the first position, the fluid pressure may be greater than the pressure threshold of the input check valve 110 causing the input check valve 110 to transition to its open state such that the fluid can transfer from the reservoir 102 to the pump 106 via the first conduit connector 103 and the input check valve 110. Also, since the fluid pressure is greater than the pressure threshold of the output check valve 112, the output check valve 112 may transition to its open state causing the fluid to transfer from the pump 106 to the inflatable member 104 via the output check valve 112 and the second conduit connector 105. This automatic transition of fluid continues until the pressure equalizes between the reservoir 102 and the inflatable member 104 (or the input check valve 110 and the output check valve 112 transition to their closed state). The automatic transfer of fluid from the reservoir 102 to the inflatable member 104 (e.g., without the user operating the pump 106) may cause a reduction in the amount of pumps to provide the desired penis rigidity. Also, with added pressure to the reservoir 102, the pump 106 can be filled at a faster rate. As such, it would allow for the feeling of penile engorgement and at least partial filling of the inflatable member 104 (e.g., the cylinders) by a single position selection of the reversing valve 108 when desired by the patient upon arousal. The full final pressurization of the inflatable member 104 may take place with subsequent pump squeezes that would be significantly fewer in number than with devices currently in use.

Further, in some examples, the reservoir 102 is pressurized such that the fluid in the reservoir 102 is transferred to the inflatable member 104 to fully inflate the inflatable member 104. In this example, the user may not have to operate the pump 106 to further inflate the inflatable member 104, but rather the inflatable member 104 can be fully (or substantially) inflated by activating the reversing valve 108 to the inflation mode. In this example, the user may use the pump 106 to deflate the inflatable member 104. In other examples, the reservoir 102 is not pressurized, but rather is a static reservoir.

In some examples, the user may operate the pump 106 to further inflate the inflatable member 104. For example, the user may repeatedly depress or squeeze the pump 106 until the desired rigidity is achieved. However, the automatic transition of fluid caused by the pressurized reservoir 102 before the user begins to operate the pump 106 may reduce the number of pump cycles. With respect to a single pump cycle, initially, both of the input check valve 110 and the output check valve 112 are closed. For example, both the input check valve 110 and the output check valve 112 may be closed at pressure equilibrium. Then, the user depresses or squeezes the pump 106 until the pressure exceeds the pressure threshold of the output check valve 112, which may cause the fluid in the pump 106 to transfer to the inflatable member 104 via the output check valve 112 and the second conduit connector 105. For example, squeezing the pump 106 may open the output check valve 112 until no volume in the pump 106 can overcome the outlet pressure. The pump 106 may then return to its original form, which provides a suction force causing the input check valve 110 to open such that fluid is transferred from the reservoir 102 to the pump 106 via the first conduit connector 103 and the input check valve 110. For example, release of the user's finger on the pump 106 may create a vacuum in the pump 106 and the input check valve 110 may open. The flow from the reservoir 102 fills the pump 106 (or at least partially fills the pump 106) until the pump's pressure is substantially equal to the reservoir's pressure. After the pump 106 returns to its original form, the input check valve 110 and the output check valve 112 may return to their closed states. This pump cycle is repeated until the desired rigidity in the inflatable member 104 is achieved.

When the user wishes to deflate the inflatable member 104, the user may operate the reversing valve 108 to switch to the second position (e.g., the deflation mode). In the second position, the reversing valve 108 may provide an open connection between the inflatable member 104 and the inlet of the input check valve 110, and an open connection between the outlet of the output check valve 112 and the reservoir 102. In the second position, in some examples, the fluid may automatically flow out of the inflatable member 104 and into the reservoir 102 without the user depressing or squeezing the pump 106 until the pressure is at least partially equalized between the reservoir 102 and the inflatable member 104.

The user may operate the pump 106 to deflate the inflatable member 104 to return the penis to a flaccid state. For example, the user may repeatedly depress or squeeze the pump 106 until the inflatable member 104 is sufficiently deflated. With respect to a single pump cycle, initially, both of the input check valve 110 and the output check valve 112 are closed. Then, the user depresses or squeezes the pump 106 until the pressure exceeds the pressure threshold of the output check valve 112, which may cause the fluid to transfer from the pump 106 to the reservoir 102 via the output check valve 112 and the first conduit connector 103. The pump 106 may then return to its original form, which provides a suction force causing the input check valve 110 to open such that the fluid is transferred from the inflatable member 104 to the pump 106 via the second conduit connector 105 and the input check valve 110. After the pump 106 returns to its original form, the input check valve 110 and the output check valve 112 may return to their closed states. This pump cycle is repeated until the inflatable member 104 is sufficiently deflated.

Figure 2:
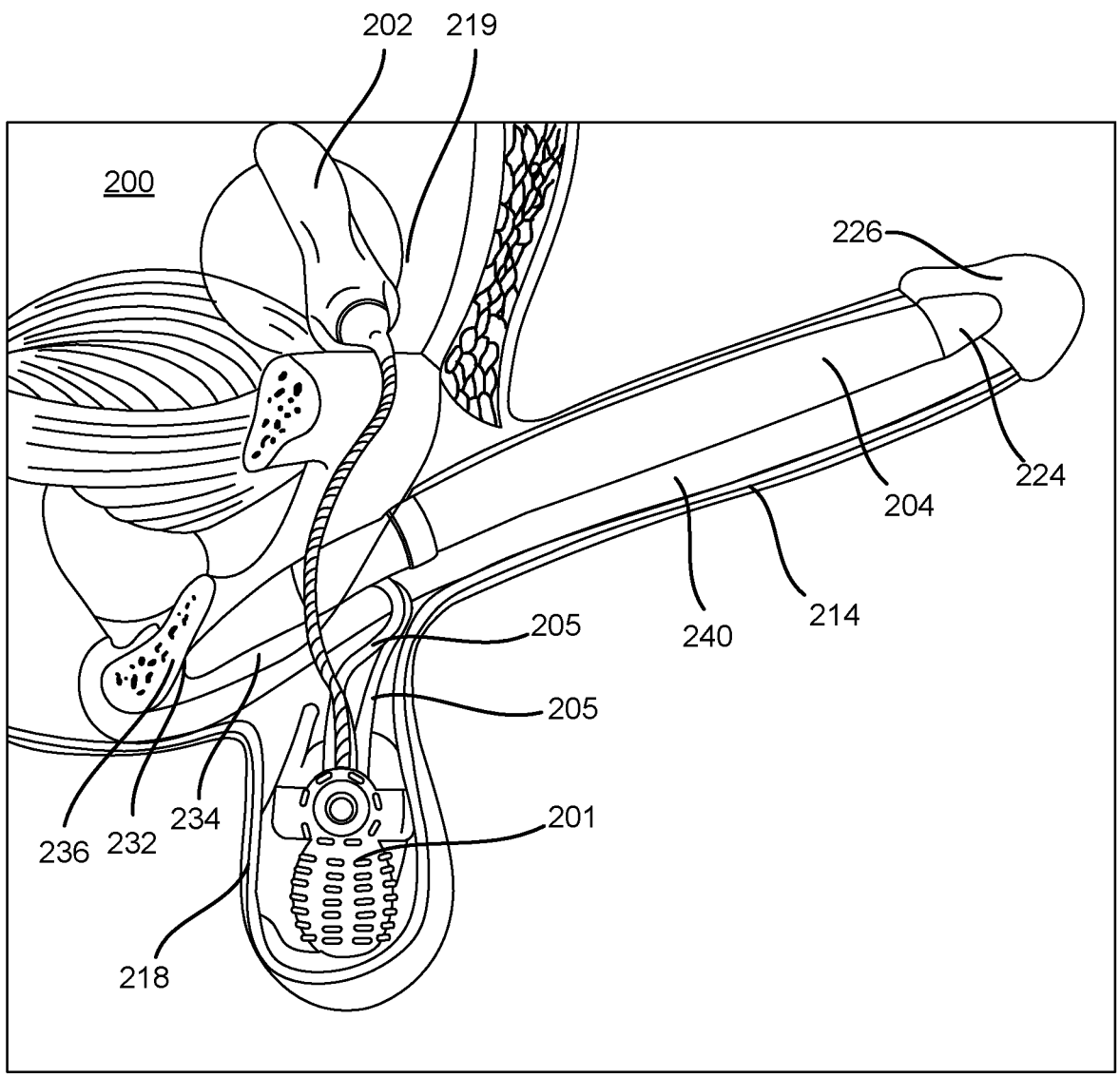
FIG. 2 illustrates an inflatable penile prosthesis according to an aspect.
Figure 3:
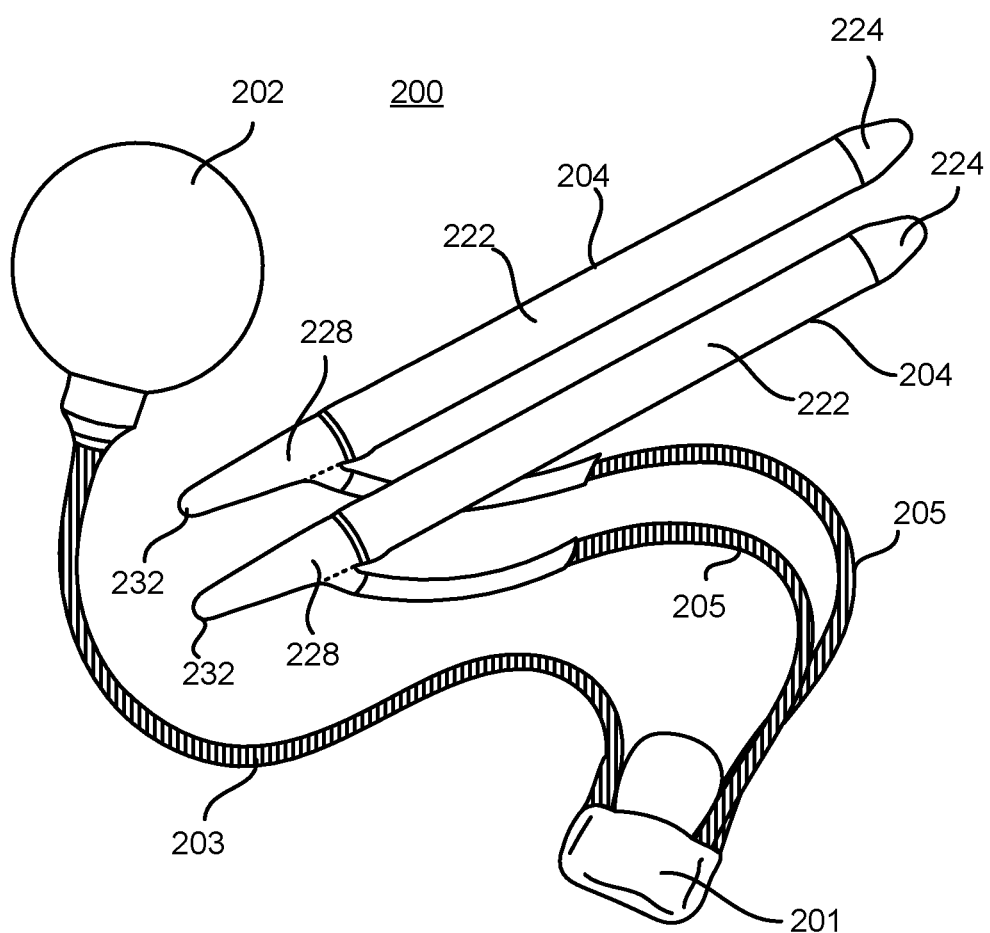
FIG. 3 illustrates an inflatable penile prosthesis according another aspect.

FIG. 2 illustrates an inflatable penile prosthesis 200 implanted within a user according to an aspect. In some examples, the inflatable penile prosthesis 200 may be the inflatable penile prosthesis 100 of FIG. 1 or include any (or any combination) of the features discussed herein with respect to any of the figures. FIG. 3 illustrates the inflatable penile prosthesis 200 having a pair of cylinders 204.

Referring to FIGS. 2-3, the inflatable penile prosthesis 200 may include a pair of cylinders 204, and the pair of cylinders 204 are implanted in a penis 214. For example, one of the cylinders 204 may be disposed on one side of the penis 214. The other cylinder 204 (not shown in FIG. 2) of the pair of cylinders may be disposed on the other side of the penis 214. The cylinder 204 may include a distal end portion 224, an inflation chamber 222, and a proximal end portion 228 having a rear tip 232.

The inflatable penile prosthesis 200 may include a reversible flow pump assembly 201, which may be implanted into the patient's scrotum 218. The reversible flow pump assembly 201 may include any of the features discussed with reference to the reversible flow pump assembly of any of the figures. A pair of conduit connectors 205 may attach the reversible flow pump assembly 201 to the pair of cylinders 204 such that the reversible flow pump assembly 201 is in fluid communication with the pair of cylinders 204. Also, the reversible flow pump assembly 201 may be in fluid communication with a reservoir 202 via a conduit connector 203, where the reservoir 202 that may be implanted into the user's abdomen 219. The inflation chamber 222 of the cylinder 204 may be disposed within the penis 214. The distal end portion 224 of the cylinder 204 may be at least partially disposed within the crown portion 226 of the penis 214. The proximal end portion 228 may be implanted into the patient's pubic region 234 with the rear tip 232 proximate the pubic bone 236.

In order to implant the cylinder 204, the surgeon first prepares the patient. The surgeon often makes an incision in the penoscrotal region, e.g., where the base of the penis 214 meets with the top of the scrotum 218. From the penoscrotal incision, the surgeon may dilate the patient's corpus cavernosae 240 to prepare the patient to receive the pair of cylinders 204. The corpus cavernosum is one of two parallel columns of erectile tissue forming the dorsal part of the body of the penis 214, e.g., two slender columns that extend substantially the length of the penis 214. The surgeon will also dilate two regions of the pubic area (proximal corpora cavernosae) to prepare the patient to receive the proximal end portion 228. The surgeon may measure the length of the proximal and distal corpora cavernosae from the incision and the dilated region of the pubic area to determine an appropriate size of the cylinder 204 to implant.

After the patient is prepared, the inflatable penile prosthesis 200 is implanted into the patient. The distal tip of the distal end portion 224 of each cylinder 204 may be attached to a suture. The other end of the suture may be attached to a needle member (e.g., Keith needle). The needle member is inserted into the incision and into the dilated corpus cavernosum. The needle member is then forced through the crown of the penis 214. The surgeon tugs on the suture to pull the cylinder 204 into the corpus cavernosum. This is done for each cylinder of the pair of cylinders 204. Once the inflation chamber 222 is in place, the surgeon may remove the suture from the distal tip. The surgeon then inserts the proximal end portion 228. The surgeon inserts the rear end of the cylinder 204 into the incision and forces the proximal end portion 228 toward the pubic bone 236 until each cylinder 204 is in place.

Figure 4A:
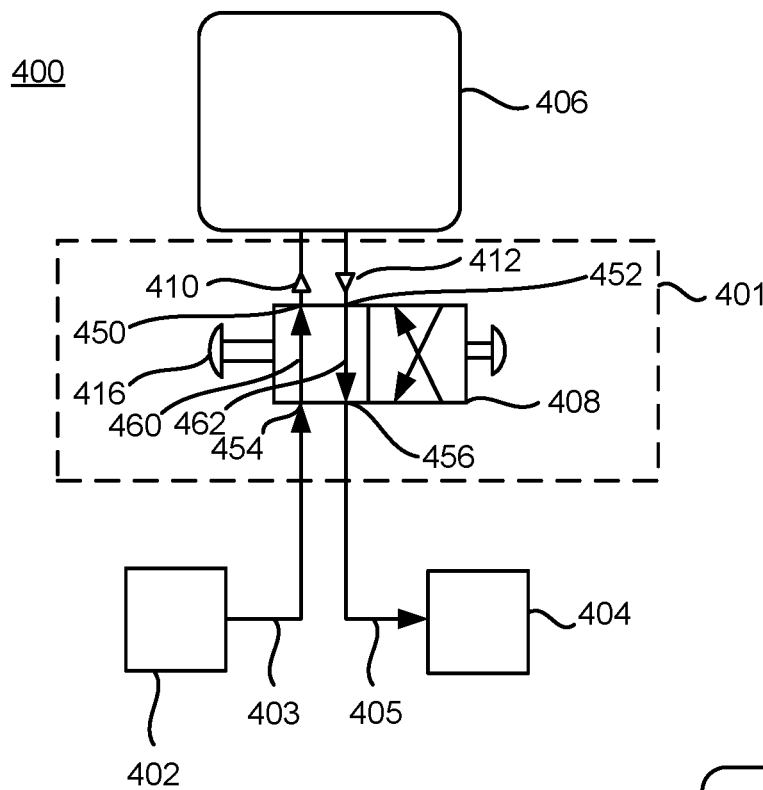
FIG. 4A illustrates an inflatable penile prosthesis with a reversible flow pump assembly in an inflation mode according to an aspect.
Figure 4B:
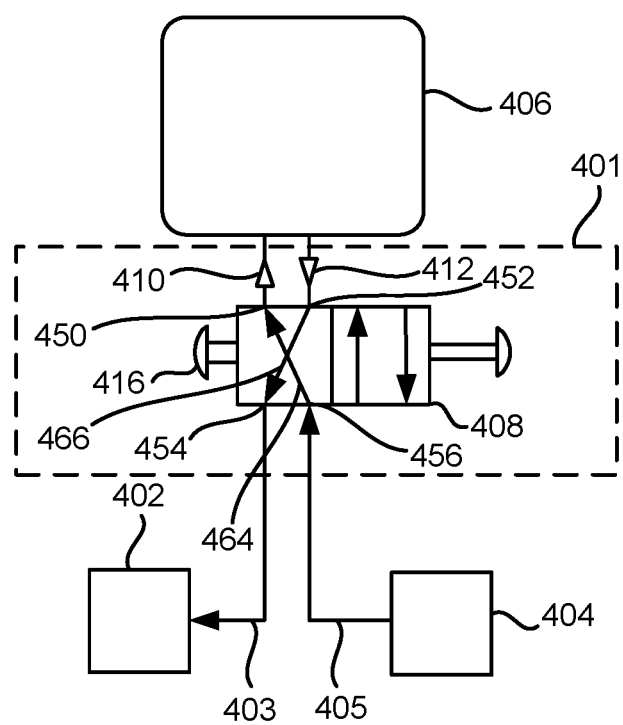
FIG. 4B illustrates the inflatable penile prosthesis with the reversible flow pump assembly in a deflation mode.

FIG. 4A illustrates an inflatable penile prosthesis 400 with a reversible flow pump assembly 401 in an inflation mode according to an aspect. FIG. 4B illustrates the inflatable penile prosthesis 400 with the reversible flow pump assembly 401 in a deflation mode. The inflatable penile prosthesis 400 may include a reservoir 402, an inflatable member 404, a first conduit connector 403, a second conduit connector 405, and the reversible flow pump assembly 401. The reversible flow pump assembly 401 may transfer fluid between the reservoir 402 and the inflatable member 404 via the first conduit connector 403 and the second conduit connector 405. In some examples, the inflatable member 404 may be implanted into the corpus cavernosae of the user, the reservoir 402 may be implanted in the abdomen of the user, and the reversible flow pump assembly 401 may be implanted in the scrotum of the user.

The reservoir 402, the inflatable member 404, the first conduit connector 403, the second conduit connector 405, and the reversible flow pump assembly 401 may include any of the features (or any combination thereof) of the reservoir 102, the inflatable member 104, the first conduit connector 103, the second conduit connector 105, and the reversible flow pump assembly 101 of FIG. 1. As such, the details of these components will be omitted for the sake of brevity. However, the description of FIG. 4 will further describe the reversible flow pump assembly 401.

The reversing valve 408 may include a mode actuator 416. The mode actuator 416 may be any type of user-operated control (e.g., switch, button, lever, etc.) having a first position in which the reversible flow pump assembly 401 is in the inflation mode (FIG. 4A), and a second position in which the reversible flow pump assembly 401 is in the deflation mode (FIG. 4B). In some examples, the reversing valve 408 includes a spool valve that allows the flow of fluid into different paths from the reservoir 402 and the inflatable member 404. In some examples, the reversing valve 408 configured as the spool valve includes a spool inside a cylinder which is mechanically (or electrically controlled), where the movement of the spool restricts or permits the flow. In some examples, the reversing valve 408 may move or slide from the first position to the second position (and vice versa).

In some examples, the reversing valve 408 may include a four-port valve. For example, the reversing valve 408 may define a first port 450, a second port 452, a third port 454, and a fourth port 456. However, in some examples, the reversing valve 408 may include more than four ports such as a five-port valve or a six-port valve. The first port 450 may be connected to the inlet of an input check valve 410, the second port 452 may be connected to the outlet of an output check valve 412, the third port 454 may be coupled to the reservoir 402 via the first conduit connector 403, and the fourth port 456 may be connected to the inflatable member 404 via the second conduit connector 405.

The user may operate the mode actuator 416 to switch between the inflation mode and the deflation mode causing the flow connections between the ports 450, 452, 454, 456 to switch, thereby enabling the reversible flow pump assembly 401 to reverse the flow direction. For example, when the user wishes to inflate the inflatable member 404, the user may operate the mode actuator 416 on the reversing valve 408 to switch to the first position (e.g., the inflation mode). Referring to FIG. 4A, in the first position, the reversing valve 408 may provide a first flow connection 460 from the third port 454 to the first port 450, and a second flow connection 462 from the second port 452 to the fourth port 456. In some examples, the first flow connection 460 may be a channel that allows the transfer of fluid from the third port 454 to the first port 450, and the second flow connection 462 may be a channel that allows the transfer of fluid from the second port 452 to the fourth port 456. As a result, when the mode actuator 416 is in the first position, the reversing valve 408 may allow transfer of the fluid from the reservoir 402 to the pump 406 via the first flow connection 460 and the input check valve 410, and allow the transfer of the fluid from the pump 406 to the inflatable member 404 via the second flow connection 462 and the output check valve 412.

In the first position, if the reservoir 402 is at least partially pressurized, the fluid may automatically flow out of the reservoir 402 and into the inflatable member 404 without the user depressing or squeezing the pump 406 until the pressure is at least partially equalized between the reservoir 402 and the inflatable member 404. In particular, after the reversing valve 408 is switched to the first position, the fluid pressure may be greater than the pressure threshold of the input check valve 410 causing the input check valve 410 to transition to its open state such that the fluid can transfer from the reservoir 402 to the pump 406 via the first conduit connector 103, the first flow connection 460 and the input check valve 410. Also, since the fluid pressure is greater than the pressure threshold of the output check valve 412, the output check valve 412 may transition to its open state causing the fluid to transfer from the pump 406 to the inflatable member 404 via the output check valve 412, the second flow connection 462, and the second conduit connector 405. This automatic transition of fluid continues until the pressure equalizes between the reservoir 402 and the inflatable member 404 and/or the input check valve 410 and the output check valve 412 transitions to their closed state.

Then, the user may operate the pump 406 to further inflate the inflatable member 404. For example, the user may repeatedly depress or squeeze the pump 406 until the desired rigidity is achieved. However, the automatic transition of fluid caused by the pressurized reservoir 402 before the user begins to operate the pump 406 may reduce the number of pump cycles. With respect to a single pump cycle, initially, both of the input check valve 410 and the output check valve 412 are closed. Then, the user depresses or squeezes the pump 406 until the pressure exceeds the pressure threshold of the output check valve 412, which may cause the fluid in the pump 406 to transfer to the inflatable member 404 via the second flow connection 462, the output check valve 412, and the second conduit connector 405. The pump 406 may then return to its original form, which provides a suction force causing the input check valve 410 to open such that fluid is transferred from the reservoir 402 to the pump 406 via the first conduit connector 403, the first flow connection 460, and the input check valve 410. After the pump 406 returns to its initial form, the input check valve 410 and the output check valve 412 may return to their closed states. This pump cycle is repeated until the desired rigidity in the inflatable member 404 is achieved.

When the user wishes to deflate the inflatable member 404, the user may operate the mode actuator 416 on the reversing valve 408 to switch to the second position (e.g., the deflation mode). The switching from the first position to the second position causes the first flow connection 460 and the second flow connection 462 to be crossed, thereby defining a third flow connection 464 from the fourth port 456 to the first port 450, and a fourth flow connection 466 from the second port 452 to the third port 454. In some examples, the third flow connection 464 may be a channel that allows the transfer of fluid from the fourth port 456 to the first port 450, and the fourth flow connection 466 may be a channel that allows the transfer of fluid from the second port 452 to the third port 454. As a result, when the mode actuator 416 is in the second position, the reversing valve 408 may allow transfer of the fluid from the inflatable member 404 to the pump 406 via the second conduit connector 405, the third flow connection 464, and the input check valve 410, and allow the transfer of the fluid from the pump 406 to the inflatable member 404 via the output check valve 412, the fourth flow connection 466, and the first conduit connector 403.

The user may operate the pump 406 to deflate the inflatable member 404 to return the penis to a flaccid state. For example, the user may repeatedly depress or squeeze the pump 406 until the inflatable member 404 is sufficiently deflated. With respect to a single pump cycle, initially, both of the input check valve 410 and the output check valve 412 are closed. Then, the user depresses or squeezes the pump 406 until the pressure exceeds the threshold of the output check valve 412, which may cause the fluid to transfer from the pump 406 to the reservoir 402 via the output check valve 412, the fourth flow connection 466, and the first conduit connector 403. The pump 406 may then return to its original form, which provides a suction force causing the input check valve 410 to open such that the fluid is transferred from the inflatable member 404 to the pump 406 via the second conduit connector 405, the third flow connection 464, and the input check valve 410. After the pump 406 returns to its original form, the input check valve 410 and the output check valve 412 may return to their closed states. This pump cycle is repeated until the inflatable member 404 is sufficiently deflated.

Figure 5:
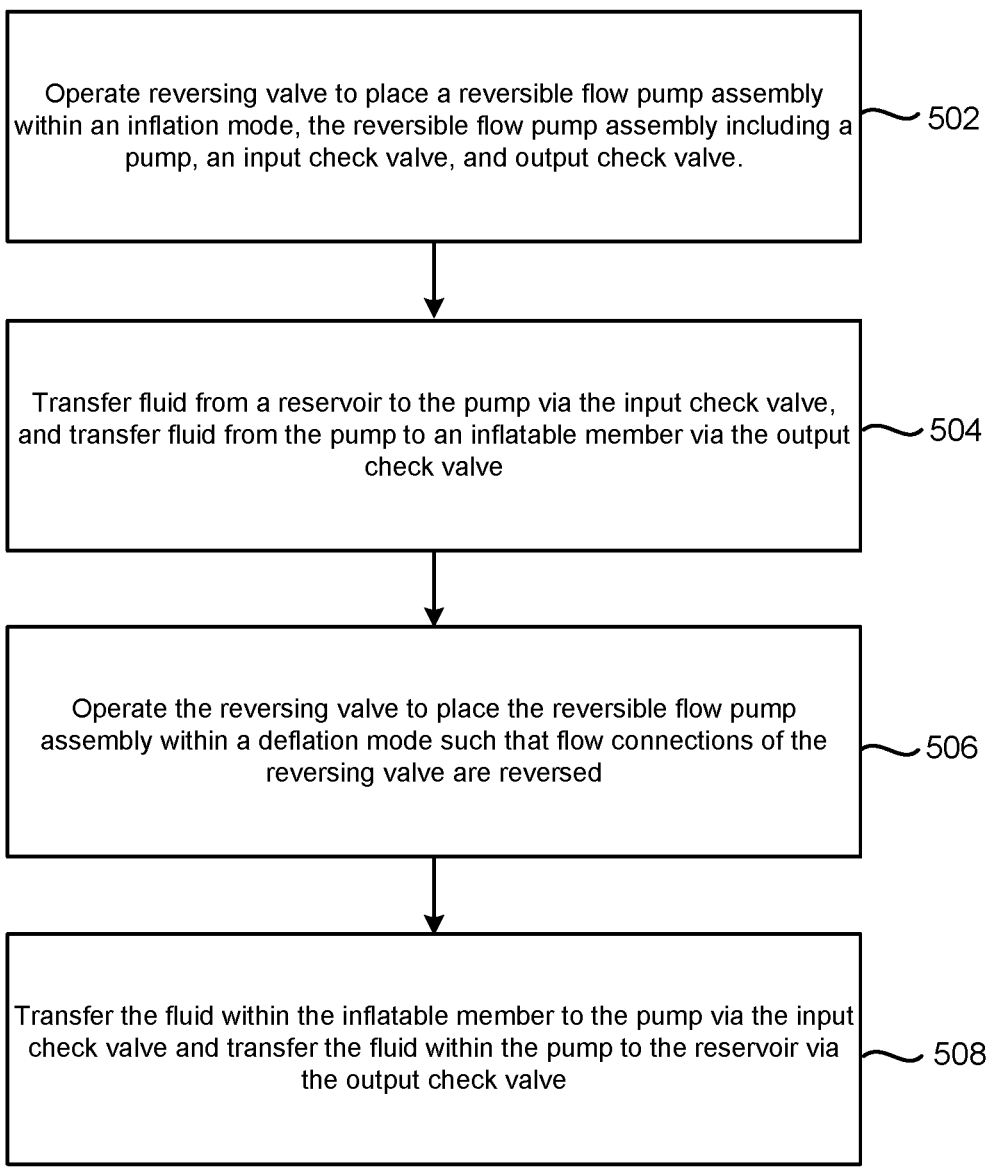
FIG. 5 illustrates a flow chart depicting a method for operating an inflatable penile prosthesis with a reversible flow pump assembly.

FIG. 5 is a flow chart for a method 500 of operating an inflatable penile prosthesis according to an aspect. The operations of the method 500 are explained with reference to the inflatable penile prosthesis 100 of FIG. 1. However, it is noted that the operations of the method 500 may be performed with any of the inflatable penile prostheses described herein including the inflatable penile prosthesis 200 and/or the inflatable penile prosthesis 400.

A reversing valve may be operated to place a reversible flow pump assembly within an inflation mode, where the reversible flow pump assembly includes a pump, an input check valve, and an output check valve (502). For example, the reversing valve 108 may be operated to place the reversible flow pump assembly 101 within the inflation mode. As described above, the reversible flow pump assembly 101 may include the reversing valve 108, the input check valve 110, the output check valve 112, and the pump 106.

Fluid from a reservoir may be transferred to the pump via the input check valve, and the fluid from pump may be transferred to an inflatable member via the output check valve (504). For example, the reversible flow pump assembly 101 may be configured to transfer the fluid from the reservoir 102 to the pump 106 via the input check valve 110, and transfer the fluid from the pump 106 to the inflatable member 104 via the output check valve 112. The input check valve 110 may serve as the only input in which fluid can enter the pump 106, and the output check valve 112 may serve as the only output in which fluid can exit the pump 106. The reversing valve 108 may define the flow connections from the reservoir 102/the inflatable member 104 to the input check valve 110/the output check valve 112. For instance, when the reversing valve 108 is within the inflation mode, the reversing valve 108 may define a flow connection providing a channel such that the reservoir 102 is within fluid communication with the input check valve 110, and define a flow connection providing a channel such that the output check valve 112 is within fluid communication with the inflatable member 104.

In some examples, the reservoir 102 is at least partially pressurized such that, upon activation to the inflation mode, the fluid from the reservoir 102 can be automatically transferred to the inflatable member 104 via the reversible flow pump assembly 101 without operating the pump 106. For example, the fluid may flow into the inflatable member 104 until the pressure across the inflatable member 104 and the reservoir 102 equalizes. Then, the user may operate the pump 106 (e.g., depress or squeeze the pump 106) for a certain amount of pump cycles until the desired rigidity is achieved. However, the automatic transfer of fluid may reduce the number of pump cycles that otherwise would be required to provide the same rigidity.

The reversing valve may be operated to place the reversible flow pump assembly within a deflation mode such that the flow connections of the reversing valve are reversed (506). For example, the reversing valve 108 may be operated to place the reversible flow pump assembly 101 within the deflation mode such that the flow connections of the reversing valve are reversed. Upon switching to the deflation mode, the reversing valve 108 may provide a flow connection from the inflatable member 104 to the input check valve 110, and a flow connection from the output check valve 112 and the reservoir 102.

The fluid within the inflatable member may be transferred to the pump via the input check valve, and the fluid within the pump may be transferred to the reservoir via the output check valve (508). For example, the reversible flow pump assembly 101 may transfer the fluid within the inflatable member 104 to the pump 106 via the input check valve 110, and transfer the fluid within the pump 106 to the reservoir 102 via the output check valve 112.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:
1. An inflatable penile prosthesis comprising:
an inflatable member;
a reservoir configured to hold fluid, the reservoir including an expandable balloon configured to pressurize the fluid in the reservoir; and
a reversible flow pump assembly configured to facilitate a transfer of the fluid from the reservoir to the inflatable member when in an inflation mode, and facilitate the transfer of the fluid from the inflatable member to the reservoir when in a deflation mode, the reversible flow pump assembly including:
a pump;
a first check valve coupled to the pump, the first check valve configured to permit transfer of fluid into the pump;
a second check valve coupled to the pump, the second check valve configured to permit transfer of fluid out of the pump;
a reversing valve configured to switch between the inflation mode and the deflation mode, the reversing valve including a first port, a second port, a third port, and a fourth port, the first port being fluidly connected to an inlet of the first check valve, the second port being fluidly connected to an outlet of the second check valve, the third port being fluidly connected to the reservoir, and the fourth port being fluidly connected to the inflatable member; and
an actuator having a first position in which the reversible flow pump assembly being in the inflation mode and a second position in which the reversible flow pump assembly being in the deflation mode,
wherein, in the first position, the first check valve is configured to operate fluid transfer from the reservoir to the pump,
wherein, in the second position, the second check valve is configured to operate fluid transfer from the pump to the reservoir.

2. The inflatable penile prosthesis of claim 1, wherein the reservoir is pressurized such that activation of the reversing valve to the inflation mode causes at least a portion of the fluid to transfer from the reservoir to the inflatable member through the reversible flow pump assembly without operating the pump.

3. The inflatable penile prosthesis of claim 1, wherein, when the reversing valve is in the inflation mode, the pump is configured to be depressed causing the fluid to transfer from the reservoir to the inflatable member through the reversible flow pump assembly.

4. The inflatable penile prosthesis of claim 1, wherein activation of the reversing valve to the deflation mode causes at least a portion of the fluid to transfer from the inflatable member to the reservoir through the reversible flow pump assembly without operating the pump.

5. The inflatable penile prosthesis of claim 1, wherein, when the reversing valve is in the deflation mode, the pump is configured to be depressed causing the fluid to transfer from the inflatable member to the reservoir through the reversible flow pump assembly.

6. The inflatable penile prosthesis of claim 1, wherein the inflatable member includes at least two cylinders.

7. The inflatable penile prosthesis of claim 1, wherein the first check valve includes a one-directional pressure valve.

8. The inflatable penile prosthesis of claim 1, wherein the second check valve includes a one-directional pressure valve.

9. The inflatable penile prosthesis of claim 1, wherein, when the reversing valve is in the inflation mode, the reversing valve provides a first flow connection between the third port to the first port such that the fluid can be transferred from the reservoir into the pump via the first flow connection and the first check valve, and a second flow connection between the second port and the fourth port such that the fluid can be transferred from the pump to the inflatable member via the second check valve and the second flow connection.

10. The inflatable penile prosthesis of claim 9, wherein, when the reversing valve is switched to the deflation mode, the reversing valve is configured to switch the first and second flow connections such that the inflatable member is within fluid communication with the first check valve and the second check valve is within fluid communication with the reservoir.

11. An inflatable penile prosthesis comprising:
an inflatable member;
a reservoir configured to hold fluid, the reservoir including elastic walls configured to pressurize the fluid in the reservoir; and
a reversible flow pump assembly configured to facilitate a transfer of the fluid from the reservoir to the inflatable member when in an inflation mode, and facilitate the transfer of fluid from the inflatable member to the reservoir when in a deflation mode, the reversible flow pump assembly including a first check valve, a second check valve, a pump, and a reversing valve having a first port, a second port, a third port, and a fourth port, the first port being fluidly connected to an inlet of the first check valve, the second port being fluidly connected to an outlet of the second check valve, the third port being fluidly connected to the reservoir, and the fourth port being fluidly connected to the inflatable member,
wherein when the reversible flow pump assembly is actuated in the inflation mode, the first check valve is configured to operate fluid transfer from the reservoir to the pump,
wherein when the reversible flow pump assembly is actuated in the deflation mode, the second check valve is configured to operate fluid transfer from the pump to the reservoir.

12. The inflatable penile prosthesis of claim 11, wherein the fluid transfers from the pressurized reservoir to the inflatable member until fluid pressure substantially equalizes between the pressurized reservoir and the inflatable member.

13. The inflatable penile prosthesis of claim 11,
wherein the first check valve is coupled to the pump, the first check valve configured to permit transfer of fluid into the pump;
wherein the second check valve coupled to the pump, the second check valve configured to permit the transfer of fluid out of the pump; and
wherein the reversing valve is configured to switch between the inflation mode and the deflation mode.

14. The inflatable penile prosthesis of claim 11,
wherein, when the reversing valve is in the inflation mode, the reservoir is fluidly coupled to the first check valve, and the inflatable member is fluidly coupled to the second check valve,
wherein, when the reversing valve is in the deflation mode, the reservoir is fluidly coupled to the second check valve, and the inflatable member is fluidly coupled to the first check valve.

15. A method for operating an inflatable penile prosthesis, the method comprising:
operating a reversing valve to place a reversible flow pump assembly in at least an inflation mode or a deflation mode, the reversible flow pump assembly including a pump, a first check valve being of a first-type valve, and a second check valve being of a second-type valve being different than the first-type valve, the reversible flow pump including at least a first port and a second port that are configured to transfer fluid in an inflation direction or a deflation direction, the inflatable penile prosthesis including reservoir including a diaphragm configured to pressurize the fluid in the reservoir;
transferring fluid within a reservoir to the pump via an inlet of the first check valve through the first port; and
transferring the fluid within the pump to an inflatable member via an outlet of the second check valve through the second port,
wherein when the reversible flow pump assembly is actuated in the inflation mode, the first check valve is configured to operate fluid transfer from the reservoir to the pump,
wherein when the reversible flow pump assembly is actuated in the deflation mode, the second check valve is configured to operate fluid transfer from the pump to the reservoir.

16. The method of claim 15, further comprising:
operating the reversing valve to place the reversible flow pump assembly in a deflation mode such that flow connections of the reversing valve are reversed;
transferring the fluid within the inflatable member to the pump via the first check valve; and
transferring the fluid within the pump to the reservoir via the second check valve.

17. The method of claim 15, wherein at least a portion of the fluid is transferred from the reservoir to the inflatable member via the reversible flow pump assembly without operating the pump.

* * * * *